US00PP08275P

United States Patent [19]

Dehan

[11] Patent Number: Plant 8,275

[45] Date of Patent: Jun. 22, 1993

[54] IMPATIENS PLANT NAMED DANOVA

[75] Inventor: Klara Dehan, Holon, Israel

[73] Assignee: Danziger — "Dan" Flower Farm, Mishmar Hashiva, Israel

[21] Appl. No.: 743,126

[22] Filed: Aug. 9, 1991

[51] Int. Cl.[5] ..... A01H 5/00
[52] U.S. Cl. ..... Plt./87.6
[58] Field of Search ..... Plt./87.6

[56] References Cited

U.S. PATENT DOCUMENTS

P.P. 6,306 9/1988 Drewlow ..... Plt. 87.6

*Primary Examiner*—James R. Feyrer
*Attorney, Agent, or Firm*—Foley & Lardner

[57] ABSTRACT

A new cultivar of Impatiens plant named Danova characterized by its varigated flowers, including a light reddish pink main color and a darker red at the base of the petals and in the main portions of certain of the petals, dark green foliage, compact growth habit, and excellent branching.

1 Drawing Sheet

The present invention relates to a new and distinctive cultivar of Impatiens plant, botanically known as Impatiens, and known by the cultivar name Danova. Danova was developed by me through controlled breeding by crossing the cultivar identified by breeding number N-15 as the female parent with the cultivar designated 38-123 as the male parent. Both parents are unreleased, proprietary lines.

Asexual reproduction of Danova by cuttings taken by applicant at Mishmar Hashiva, Israel, has shown that the unique features of this new Impatiens are stabilized and are reproduced true to type in successive propagations. The cuttings preferably comprise tip cuttings with at least one axillary bud, which is vegatative and not a flower bud.

The following characteristics distinguish the new Impatiens from both its parent varieties and other cultivated Impatiens of this type known and used in the floriculture industry:

1. Variegated flowers, with the main color being a light reddish pink and a second darker color appearing at the base of the petals and to varying degrees on certain of the petals. The veriegated color sometimes occurs as dots and in other instances it may be the dominant color of the petal.
2. The leaves are very dark green tending toward purple.
3. Compact growth habit.
4. Excellent branching.
5. Purple stems.

The accompanying color photographs illustrate the overall appearance of this cultivar, showing the colors as true as it is reasonably possible to obtain in a colored reproduction of this type. The top photo comprises a top perspective of a portion of a plant of Danova. The bottom photograph comprises a close up view of a single flower.

The following is a detailed description of my new impatiens cultivar based on plants produced under commercial practice in the spring in Mishmar Hashiva, Israel.

Color references are made to The Royal Horticultural Society Colour Chart except where general terms of ordinary dictionary significance are used.

Parentage:

*Male parent.*—38-123.

*Female parent*—N-15.

Propagation:

A. *Type cutting.*—Tip cuttings with at least one axillary, vegetative bud.

B. *Time to initiate roots:* 8–10 days both at 25°–30° C. summer, and 20°–25° C. winter.

C. *Rooting habit:* Good root initiation.

Plant Description:

A. *Form.*—Mounded, with dense showing of flowers.

B. *Habit of growth.*—Compact with excellent branching.

C. *Foliage description.*—(1) Size: Approximately 8.5 cm long and 3.5 cm wide. (2) Shape: Oval with acuminate tip. (3) Margin: Finely serrated. (4) Color: Mature foliage top side very dark green heavily infused with purple, the color of the underside of the leaves; precise color value connot be ascertained due to extend of such color infusion; underside, mature foliage 187A-187B. (5) Venation: Purple.

Flowering description:

A. *Flowering habits.*—Opening of flowers from buds takes about five days.

B. *Natural flowering season.*—Natural flowering is in the spring and summer. In Israel it will also flower in the winter. Flowering is continuous at temperatures above approximately 10° C. and with at least minimum levels of light.

C. *Flower buds.*—Normal. Spurs up to 3.5 cm long on mature buds with throat originating from major sepal; the oval part of the spur is 0.9 cm by 0.6 cm and close to 50A in color; the long part is approximately 3.0 cm in length, almost straight, and red infused with green 145A.

D. *Flowers borne.*—Flower buds are presented at the tips of stems overlying the terminal whorls of leaves. At most stems, there are generally about 4–5 buds in different stages of maturity, and normally about 1–2 or more open blooms, as the plant reaches market stage.

E. *Quantity of flowers.*—Total inflorescence is about 20–30 simultaneously open flowers 3 months after planting.

F. *Petals.*—(1) Shape: Two pairs of heart shaped petals and one single. (2) Color: Top side in spring when opening 50D (main color) variegated with 33A at base and over substantial parts of some petals; main color fades to 56A; underside 33B with some fading on maturity. (3) Number of petals: Five. (4) Size of flowers: Approximately 5.0 cm in diameter.

G. *Reproductive organs.*—(1) Stamens: One in number. (a) Anther color: Green and purple. (b)

Pollen color: White (2) Pistils: (a) Stigma: Cone shaped; light green in color. (b) Style: Light Green in color. (c) Ovaries: One in number; size 1.5 mm; color light green.

Disease resistance: None to date.

Other important characteristics: The color of the stems is purple.

I claim:

1. A new and distinct cultivar of Impatiens named Danova, as illustrated and described.

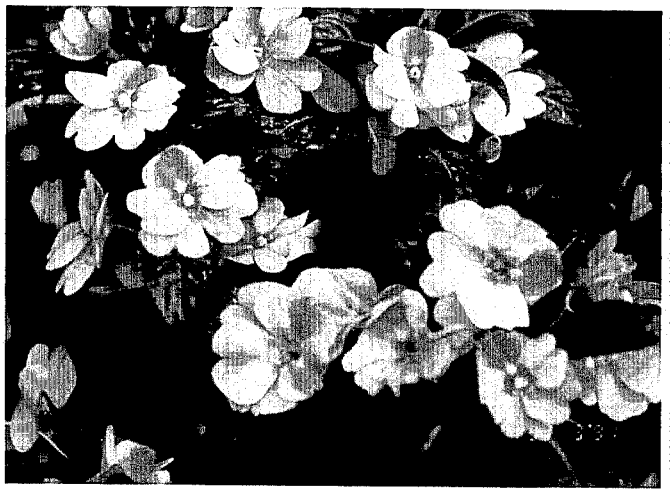
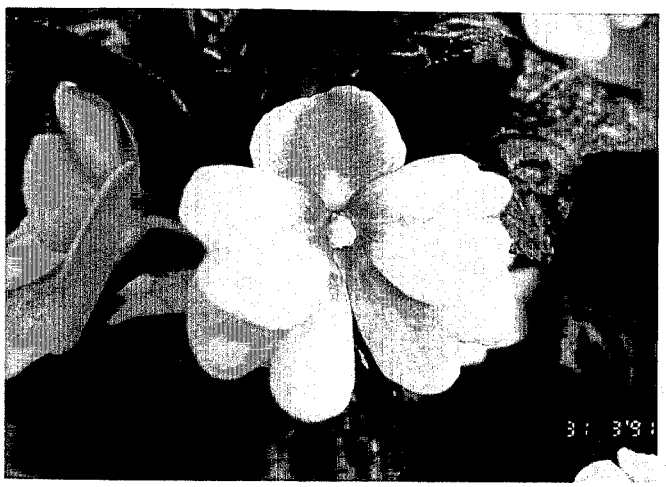

* * * * *